United States Patent [19]
Trotta

[11] Patent Number: 5,620,649
[45] Date of Patent: Apr. 15, 1997

[54] PUNCTURE RESISTANT BALLOON CATHETER

[75] Inventor: Thomas Trotta, Miami, Fla.

[73] Assignee: Cordis Corporation, Miami Lakes, Fla.

[21] Appl. No.: 540,781

[22] Filed: Oct. 11, 1995

Related U.S. Application Data

[60] Division of Ser. No. 189,496, Jan. 31, 1994, Pat. No. 5,478,320, which is a continuation-in-part of Ser. No. 442,568, Nov. 29, 1989, Pat. No. 5,290,306.

[51] Int. Cl.⁶ ................................................. B29C 49/22
[52] U.S. Cl. ............................ 264/515; 604/96; 606/194
[58] Field of Search ............................ 264/515, 171.28; 604/96; 606/194; 428/35.7, 36.6, 36.91; 215/12.1, 12.2

[56] References Cited

U.S. PATENT DOCUMENTS

| | | |
|---|---|---|
| 3,045,677 | 7/1962 | Wallace . |
| 3,814,137 | 6/1974 | Martinez . |
| 3,889,685 | 6/1975 | Miller, Jr. et al. . |
| 3,924,634 | 12/1975 | Taylor et al. . |
| 3,997,383 | 12/1976 | Bieler et al. ........................ 264/171.28 |
| 4,141,364 | 2/1979 | Schultze . |
| 4,174,783 | 11/1979 | Abe et al. .............................. 215/12.1 |

(List continued on next page.)

FOREIGN PATENT DOCUMENTS

| | | |
|---|---|---|
| 0420488 | 4/1991 | European Pat. Off. . |
| 0457456 | 11/1991 | European Pat. Off. . |
| 55-91634 | 7/1980 | Japan ..................................... 264/515 |

OTHER PUBLICATIONS

"Expandable Intrahepatic Portacaval Shunt Stents," Palmaz et al. AJR: 145, pp. 821–825, Oct. 1985.

"Expandable Intraluminal Graft: A Preliminary Study," Palmaz et al., vol. 156, No. 1, pp. 73–77.

"The Palmaz Stent: A Possible Technique for Prevention of Postangioplasty Restenosis," Levin, vol. 169, pp. 873–874, Radiology, Sep. 1988.

Ser. No. 362,251 Jun. 1987.

Data Sheet pertaining to PLEXAR—Extrudable Tier Layer Resin Sold by Quantum—1 page.

Data Sheets pertaining to PLEXAR—Tie–Layer Resins—The Essential Bond for Coextruded Packaging—Sold by Quantum—8 pages.

Data Sheet pertaining to PLEXAR—Tie–Layer Resin—Designing PLEXAR Tie–Layer Resins with Low MVTR Properties—Sold by Quantum—4 pages.

"Intraluminal Stents in Atherosclerotic Iliac Artery Stenosis: Preliminary Report of a Multicenter Study," Palmaz et al., vol. 168, pp. 727–731, Radiology, Sep. 1988.

Data Sheet pertaining to PLEXAR—Tie–Layer Resin—Evaluation of PLEXAR Tie–Layers of EVOH/PET Coextrusion—Sold by Quantum—2 pages.

*Primary Examiner*—Catherine Timm
*Attorney, Agent, or Firm*—Gerstman, Ellis & McMillin, Ltd.

[57] ABSTRACT

A balloon catheter comprises a flexible, elongated member, an inflatable balloon carried on the elongated member to define an inflated chamber within the balloon, and an inflation conduit extending along the member and communicating with the inflation chamber. The inflatable balloon, in turn, defines a wall which comprises at least three bonded layers. A first pair of the layers comprises a flexible plastic material which is typically a condensation polymer. A second of the layers comprises a flexible polymer which is typically a vinylic polymer which is covalently bonded to the first layers and positioned between them.

1 Claim, 1 Drawing Sheet

U.S. PATENT DOCUMENTS

| | | |
|---|---|---|
| 4,195,637 | 4/1980 | Gruntzig et al. . |
| 4,323,071 | 4/1982 | Simpson et al. . |
| 4,338,942 | 7/1982 | Fogarty . |
| 4,351,341 | 9/1982 | Goldberg et al. . |
| 4,406,656 | 9/1983 | Hattler et al. . |
| 4,479,497 | 10/1984 | Fogarty et al. . |
| 4,553,545 | 11/1985 | Maass et al. . |
| 4,573,966 | 3/1986 | Weikl et al. . |
| 4,606,347 | 8/1986 | Fogarty et al. . |
| 4,705,709 | 11/1987 | Vailancourt . |
| 4,732,152 | 3/1988 | Wallsten et al. . |
| 4,763,653 | 8/1988 | Rockey . |
| 4,776,337 | 10/1988 | Palmaz . |
| 4,795,458 | 1/1989 | Regan . |
| 4,800,882 | 1/1989 | Gianturco . |
| 4,811,737 | 3/1989 | Rydell . |
| 4,866,127 | 9/1989 | Jacquemin et al. . |
| 4,906,237 | 3/1990 | Johansson et al. . |
| 4,923,450 | 5/1990 | Maeda et al. . |
| 4,933,178 | 6/1990 | Capelli . |
| 5,185,189 | 2/1993 | Stenger et al. ............ 428/35.7 |
| 5,195,969 | 3/1993 | Wang et al. . |
| 5,270,086 | 12/1993 | Hamlin . |

PUNCTURE RESISTANT BALLOON CATHETER

CROSS REFERENCE TO RELATED APPLICATION

This is a division of application Ser. No. 08/189,469, filed Jan. 31, 1994 now U.S. Pat. No. 5,478,320 which is a continuation in part of Trotta, et al. U.S. application Ser. No. 07/442,568, filed Nov. 29, 1989, now U.S. Pat. No. 5,290,306.

BACKGROUND OF THE INVENTION

Balloon catheters are well-known devices in which the catheter carries an inflatable balloon to occlude and seal a body space, to expand a blood vessel through pressurized inflation of the balloon, or for any other desired purpose which may typically but not necessarily be a therapeutic purpose in the medical field. In the case of dilatation balloon catheters for angioplasty, for example a PTCA procedure, the catheter balloons are generally made out of thin walled, high tensile materials with relatively low resilience such as PET; a thin walled, high tensile material with tailored resilience such as nylon 12 or a thicker walled, relatively high resilience material such as polyolefin copolymers and polyethylene. In the case of high strength, thin wall materials the catheter balloon may be made out of biaxially oriented polyethylene terephthalate (PET) or a polyamide material such as nylon, specifically, nylon 12. Such strong, flexible materials are commonly used for angioplasty balloons, and have the advantage that they are flexible but inelastic so that they can expand outwardly to a predetermined diameter, and then cease further expansion at normal pressures, to avoid damage to the artery wall by overexpansion.

one difficulty which is found with such balloons is that, since they are typically very thin-walled, they can be easily punctured through abrasion or the like, even though they have a high tensile strength. Thin walled balloons made of PET are especially subject to this. Thus, pin holes and ruptures can occur when such catheter balloons are used in contact with rough surfaces. Also, tiny flaws in the mold of such balloons can create weak spots, since the balloons are so thin-walled. However, it is impractical to increase the wall thickness of these biaxially oriented, non-resilient materials, since then they become too stiff, with high flexural moduli, with the result that such balloons do not collapse properly on deflation to facilitate easy withdrawal from the vascular system of a patient. For example, balloons made of PET are sometimes protected by coating with more abrasion resistant materials. These coating materials, however, are not flexible enough, and lead to a balloon which does not fold properly.

Accordingly, there is a need for a balloon catheter in which the catheter balloon is strong and relatively inelastic, without being subject to the formation of pin holes, or tears in the balloon wall through abrasion. At the same time, the balloon must still be easily collapsible down to a small diameter upon deflation.

DESCRIPTION OF THE INVENTION

In this invention, a balloon catheter is provided which comprises a flexible, elongated tubular member, an inflatable balloon carried on the elongated member to define an inflation chamber within the balloon, and an inflation conduit extending along the member and communicating with the inflation chamber.

By this invention, the inflatable balloon defines a wall which comprises at least three coextruded layers. A first pair of the layers comprises a flexible, high strength plastic material. A second of the layers comprises a highly flexible, typically lower strength polymer which is preferably covalently bonded to the first layers and positioned between them.

The balloon of this invention may also be defined as comprising a pair of first layers made of a flexible condensation polymer, while a second layer is positioned between the first layers and comprises a vinylic polymer, preferably having functional groups chemically bonded to the first layers.

The term "condensation polymer" describes polymers which are manufactured by a condensation chemical reaction. For example, polyamides such as nylon are manufactured by a condensation reaction typically of a diamine with a dicarboxylic acid. Polyurethanes are typically made by a condensation reaction of a diisocyanate and a diol. Polyesters such as PET are typically made by a condensation reaction between a dicarboxylic acid and a diol.

On the other hand, the term "vinylic polymer" refers to those polymers which result from the polymerization of a vinyl or other unsaturated groups of a larger molecule, or the ethylene molecule itself, resulting in such polymers as polyethylene and polyethylene with pendent groups or other substituents, such as polypropylene, polyvinyl chloride, poly(ethylene-vinyl acetate), or the like.

The functional groups which are found on the vinylic polymers used in this invention for bonding may include copolymerized units such as an unsaturated carboxylic acid, or an anhydride thereof, or functional groups which are substituents of vinyl-containing molecules which are polymerized or copolymerized to form the vinylic polymer, for example hydroxyl in the case of polyvinyl alcohol. Preferably, the vinylic polymer used herein has functional groups which are part of copolymerized, unsaturated dicarboxylic acid groups such as maleic acid or maleic anhydride, present in an amount of about 1 to 5 mole percent as copolymer units.

The vinylic polymer used herein may comprise low density polyethylene, medium density polyethylene, linear low density polyethylene, or high density polyethylene, for example, with preferably on the order of about 1 or 2 mole percent copolymerized with reactive acid units such as maleic anhydride. Poly(ethylene-vinyl acetate), copolymerized with an appropriate amount of reactive acid units, may also be used in desired circumstances.

The copolymerized, unsaturated carboxylic acid or anhydride thereof thus can serve as a functional group which bonds the vinylic polymer second layer to the first layers for example, particularly when the first layer is a polyamide such as nylon or another nitrogen-containing polymer such as polyurethane. Similarly, such vinylic polymers having acid functional groups may react with hydroxyl-containing polymers of the first layer, under proper reaction conditions. Such reactions may take place during coextrusion of the two layers, to form a covalent bond between the first and the second layers of the balloon as it is formed by the extrusion.

The first, outer layers of the balloon may be made of a flexible material which is typically of less elasticity than the material of the second layer, to provide the desired function in which the catheter balloons are of limited maximum diameter. The second layer may be less stiff than the first layer, so that the presence of the second layer typically does not greatly increase the overall stiffness of the balloon.

As an advantage of the balloon catheter of this invention, the undesirable characteristic of "winging" in which the inflatable balloon collapses on deflation into an enlarged-width, flat configuration, is reduced or eliminated by the presence of the second layer which is more resilient than the first layers, without creating undue stiffness in the balloon.

At the same time, any pin holes that may have been formed in the first layers of the inflatable balloon are sealed by the second layer, so that the loss of inflation fluid through the pin hole, if it exists, will be negligible or non-existent. At the same time, the outer first layer can serve as an outer protective coating to the balloon. Also, the inner first layer inside of the second layer can protect against damage caused by internally mounted metal radiopaque rings and the like. Likewise, nylon first layers provide good balloon sealing compatibility to nylon catheter shafts.

The second layer may typically comprise a material having an elongation to break of at least about 100 percent and a Shore 'D' durometer of no more than substantially 55, to assure that the material is relatively soft and elastic. The relatively inelastic first layers, however, may have an elongation to break of typically no more than about 30 percent, preferably measured after biaxial orientation. Such materials generally are also substantially stiffer, having a Shore 'D' durometer of at least about 70.

It is also preferable for the preferred biaxially oriented first layers to have a glass transition temperature that is substantially above the body temperature (37° C.). For example, the glass transition temperature of nylon 12 is about 40° C., so that the first layer, as used with a patient, is in its glassy form. The second layer, however, preferably has a glass transition temperature which is substantially below the body temperature of 37°, so that it is in its elastic form. The above cited preferred numerical physical properties assume that both the first and second layers are respectively below and above their glass transition temperatures when measured.

Balloon pin holes in the first layer are thus sealed by the second layer with greatly increased reliability, since a pin hole will only have a negative effect if both layers exhibit aligned pin holes. Separate pin holes in any or all of the layers which do not register with each other will generally have no negative effect, since there can be no significant leakage through the walls upon balloon inflation in that circumstance since the layers are bonded together.

Typically, relatively stiff, flexible but nonelastic first layers are used for the reasons previously described, which limits the overall thickness of such first layers that can be provided to the balloon, whether or not more than one first layer is provided in the laminated layers of the balloon. However, typically the second layer does not contribute significantly to the overall balloon stiffness, so the wall thickness of the balloon can be controlled by any variation in the second layer wall thickness, whether one or more second layers are used, to control the balloon wall thickness without significantly increasing the overall stiffness thereof. This permits one to tailor the expansion properties of the balloon in accordance with U.S. Pat. No. 5,236,659 (the disclosures of which are incorporated by reference) while independently controlling the wall thickness as may be desired.

DESCRIPTION OF SPECIFIC EMBODIMENTS

Figure 1:
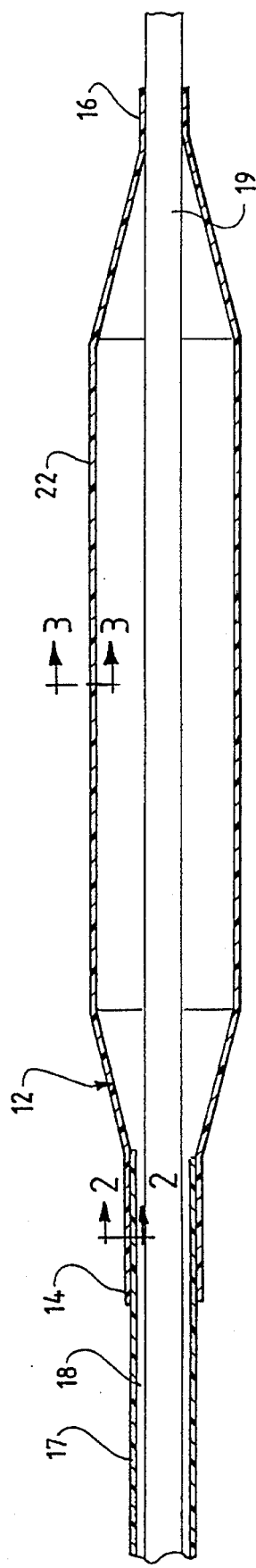
FIG. 1 is an enlarged, fragmentary view, taken partly in longitudinal section, of the distal end of a balloon catheter in accordance with this invention.
Figure 3:
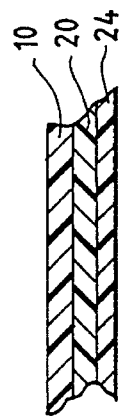
FIG. 3 is a sectional view taken along line 3—3 of FIG. 1.
Figure 2:
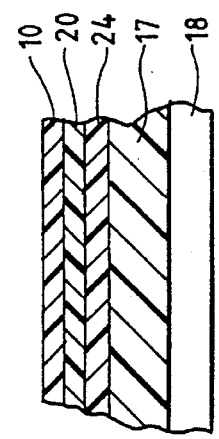
FIG. 2 is a sectional view taken along line 2—2 of FIG. 1.

In the drawing, a catheter is shown in which balloon 22 is carried at the distal end of catheter or guidewire 12, which catheter may be of any conventional design of the prior art, as modified by the disclosures herein. For example, the specific catheter shown may be used for a conventional PTCA procedure, using balloon 22 to expand the inner diameter of an occluded coronary artery. The term "catheter" is intended to include the "balloon on a wire" type device.

As is conventional, balloon 22 is sealed at its respective ends 14, 16 to an outer catheter tube 17 and an inner catheter or guidewire 19 as shown, both of which may be made of nylon for good sealing. Inflation lumen 18 may be conventionally provided for fluid inflation and deflation of balloon 22, being a space between outer catheter tube 17 and inner guidewire or catheter 19. Inner member 19 may or may not carry one or more catheter lumens, as may be desired, or, as stated, it may be in the form of a guidewire so that the entire catheter system is of the "balloon on a wire" type.

Balloon 22 may be made of a tubular multilayer plastic member. This plastic member may have a central layer 20 which may be bracketed inside and out as desired by first, outer layers 10, 24. First layers 10, 24 may each comprise a relatively stiff, non-elastic condensation polymer such as nylon 12. The second, central layer 20 is the vinylic polymer which is softer and more resilient than the condensation polymer, and which has the functional groups permitting covalent bonding with the plastic of both first layers 10 and 24. Specifically, a modified polyethylene resin may be used having pendent carboxylic acid or acid anhydride groups, as described elsewhere herein.

Such a three layer balloon may be manufactured by coextrusion, and then expansion as described in Pinchuk, et al. U.S. Pat. No. 4,906,244, the disclosures of which are incorporated herein by reference. By an extrusion process at elevated temperature, a covalent bond may be formed through the carboxylic acid or acid anhydride groups present between the second, central layer 20 and the respective first, outer layers 10, 24, to provide a plastic balloon having a multilayer wall which is flexible but not resilient because of the presence of the first layers, yet which is strongly resistant to pinholing, but not stiff so as to interfere with the desired balloon collapse. Additionally, despite the high strength and resistance to pinhole formation, balloons of this invention may exhibit sufficient flexibility to have a good capability to conform to the shape of the blood vessel in which they are placed at body temperature.

Plastic balloon 22 may have first layers 10, 24 made of nylon 12. They may each have, for example, a thickness on the order of 0.001 to 0.0001 inch, typically less than 0.001 inch. Second layer 20 may, for example, have a thickness on the order of 0.0001 to 0.002 inch and may comprise a polyethylene material which carries about 1 or 2 mole percent of copolymerized maleic anhydride groups.

Balloon 22 may be coextruded and blow molded, with the respective layers 10, 20, 24 being bonded by covalent reaction of the pendent maleic anhydride polymer units with the nylon, which contains hydrogen groups bonded to nitrogen atoms which may be reactive with the maleic anhydride.

Such modified resins for use as the second layer 20 are commercially available from the Quantum Chemical Corporation under the trademark PLEXAR, being used conventionally as tie layer resins for the bonding of dissimilar plastics together in coextruded films. Specific extrusion conditions for best bonding depend on the product used.

In this invention, however, such materials as PLEXAR resins may be used in their own right as the second layer of this invention, to coat and bond first layers of a catheter balloon, both inside and outside of the catheter balloon, to achieve the advantages previously described herein. As one advantage, sealing of the balloon to catheter tube portions may be thus facilitated.

The specific second layer 20 of this invention preferably exhibits significantly increased softness and resilience over the first layers 10, 24, with some versions of PLEXAR resins being resilient enough to qualify as true elastomers (at least 100% elongation after formation of the balloon), although other polyolefins which are not true elastomers, but have elastic characteristics, may also be used.

Furthermore, the specific, modified resins used as the second layer 20 in this invention exhibit improvements over polyurethane second layers of similar thickness, for example, in that balloons with the polyethylene second layers exhibit an unexpected advantage of ripping primarily longitudinally in the event of balloon bursting. This avoids a potential loss of a piece of the balloon, since longitudinal rips tend to permit the balloon to remain in a single piece. It is of course a significant and unfortunate problem if a piece of a burst balloon breaks loose from the remainder of the catheter, to float free in the arterial system of the patient.

Typically, the thickness of the balloon wall is from about 0.0004 to 0.003 inch. The second layer 20 comprises typically from about 10 to 80 percent of the thickness, with the balance of the thickness comprising said first layers. Preferably, the second layer 20 is no more than 50% of the overall thickness and each first layer 10, 24 is no more than 0.0004 inch thick.

EXAMPLE

A three layer tubular plastic parison was extruded, using two, one inch Genca and one and one fourth inch Genca extruders, connected to a common extrusion head (Genca tri-die cross-head). The three layer parison comprised an outer layer of nylon 12 (Huels L2101F); a middle layer of carboxyl-modified polyolefin (Quantum Plexar PX360); and an inner layer of nylon 12 (Huels L2101F). Each layer was about the same thickness. The resulting extruded parison had an outside diameter of 0.032 inch and an inside diameter of 0.021 inch.

The parison was first expanded by blow molding at 22° C. and 450 psi in a cylindrical mold of 0.088 inch inner diameter. Then the parison was given a second blow molding expansion at 125° C. and 200 in a balloon mold having an inner diameter of 0.098 inch.

The resulting balloon had a wall thickness of 0.0006 inch; a burst pressure of 275 psi; a diameter at 75 psi of 0.0101 inch; and a diameter at burst of 0.118 inch. The resulting balloon was soft enough to be easily collapsible, and compliant enough to provide good contact about its area with a lumen of irregular shape in which it is placed, such as an artery, while exhibiting high resistance to the formation of pin holes.

When the balloon is incorporated by conventional heat sealing into an angioplasty catheter of otherwise-conventional design, it is easily heat sealed into relation with the balance of nylon catheter tubing at its proximal end, and to a wire or nylon catheter tubing at its distal end, to serve as an angioplasty balloon. Particularly, the ability of such a balloon to conform to the shape of an artery under pressure is superior to biaxially oriented PET balloons, and pure nylon balloons of similar wall thickness. The presence of the second, polyolefin layer improves that characteristic.

Thus, a balloon on a catheter or guidewire is provided which exhibits significantly improved advantages as described above over prior art catheter balloons. This is done particularly by the use of polyolefins having pendent, functional bonding groups as a second, inner layer, for bonding to a condensation polymer as the first, outer layers. This provides significant advantage, including the formation of longitudinal tear lines upon rupture of the balloon.

The above has been offered for illustrative purposes only, and is not intended to limit the scope of the invention, which is as defined in the claims below.

That which is claimed is:

1. A method for manufacturing a medical balloon catheter which comprises the steps of:

providing a tubular catheter comprised of nylon;

extruding a tubular, three layer plastic parison under conditions to provide a unitary parison having at least three bonded plastic layers of flexible plastic material;

said three layer parison comprising a pair of tubular nylon layers which surround a tubular intermediate layer made of a copolymer of a major amount of ethylene and a minor amount of an unsaturated carboxylic acid or an anhydride thereof;

thereafter placing said parison into a blow mold;

thereafter expanding the diameter of said parison by causing the plastic thereof to stretch through internal blow molding pressure, said expanded diameter parison comprising a medical balloon; and thereafter attaching said medical balloon to an end of said tubular catheter.

* * * * *